United States Patent [19]
Recuset

[11] Patent Number: 5,741,286
[45] Date of Patent: Apr. 21, 1998

[54] LAPAROSCOPIC INSTRUMENT KIT INCLUDING A PLURALITY OF RIGID TUBES

[75] Inventor: Daniel Recuset, Miami, Fla.

[73] Assignee: Symbiosis Corporation, Miami, Fla.

[21] Appl. No.: 660,395

[22] Filed: Jun. 7, 1996

[51] Int. Cl.$^6$ ................................................ A61B 17/32
[52] U.S. Cl. .................................... 606/170; 606/167
[58] Field of Search ............................. 606/170, 171, 606/167, 209, 180

[56] References Cited

U.S. PATENT DOCUMENTS 5,152,744  10/1992  Krause et al. ...................... 606/170
5,527,326  6/1996  Hermann et al. .................... 606/170

*Primary Examiner*—Michael Buiz
*Assistant Examiner*—Kevin Truong
*Attorney, Agent, or Firm*—David P. Gordon

[57] ABSTRACT

A laparoscopic surgical instrument includes an actuation handle, a control member, a flexible tube, a rigid tube, and an end effector assembly. The control member extends through the flexible tube, and the actuation handle is coupled to the control member and the flexible tube. The end effector assembly is coupled to the control member and the flexible tube. The actuation handle is arranged to move the control member relative to the flexible tube, resulting in the operation of the end effector assembly. The rigid tube extends over the flexible tube and conforms the flexible tube to the shape and curve of the rigid tube. A set of rigid tubes, each curved to varying degrees, may be provided, wherein each tube may extend over the flexible tube and be removably coupled to the handle. The practitioner is able to choose from the variety of rigid tubes the tube which is most appropriate for a procedure. The practitioner is further able to change the instrument from one having a rigid tube of a first curvature to one having a rigid tube of a second curvature by uncoupling a first rigid tube and coupling a second rigid tube more appropriate for a given portion of a procedure.

20 Claims, 6 Drawing Sheets

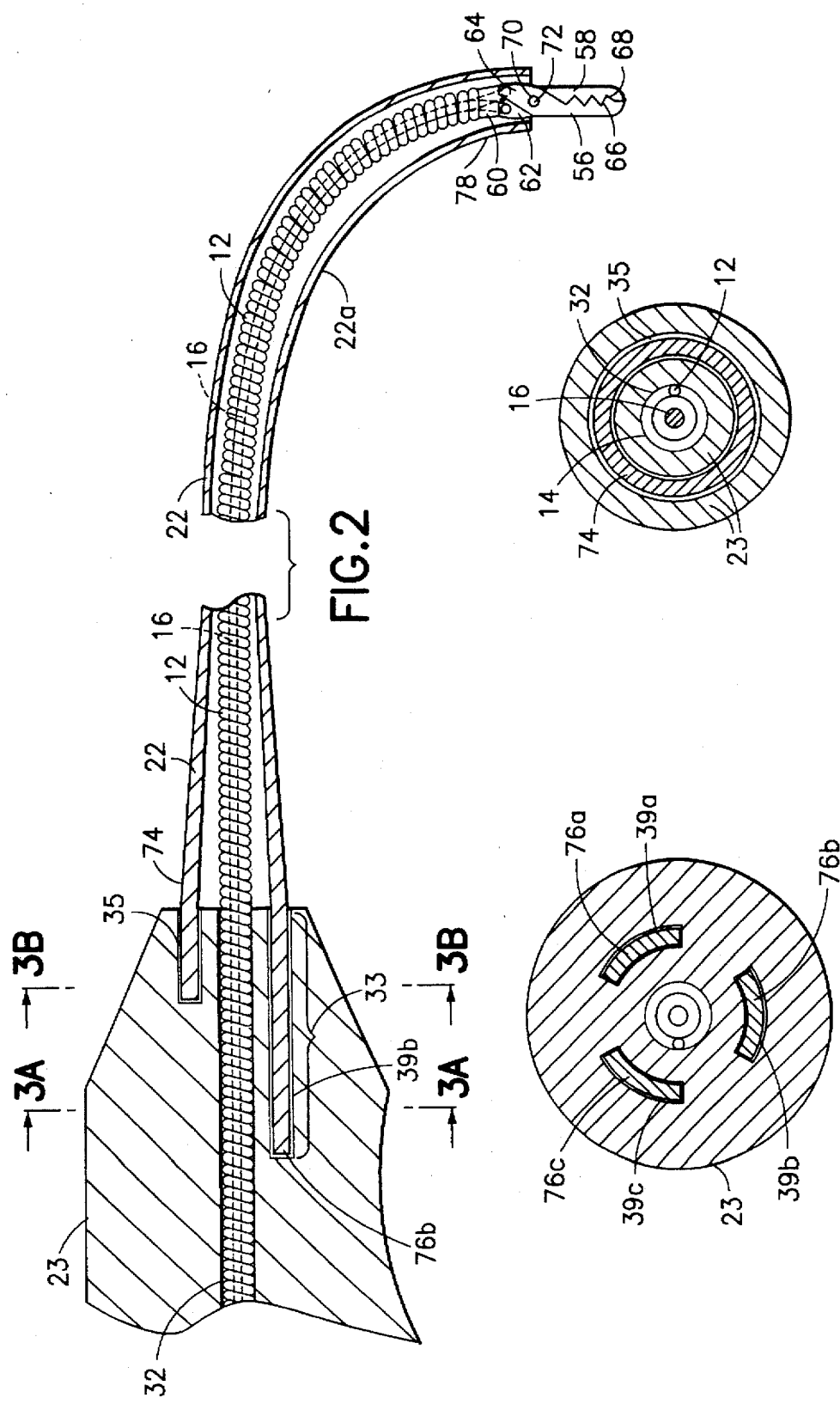

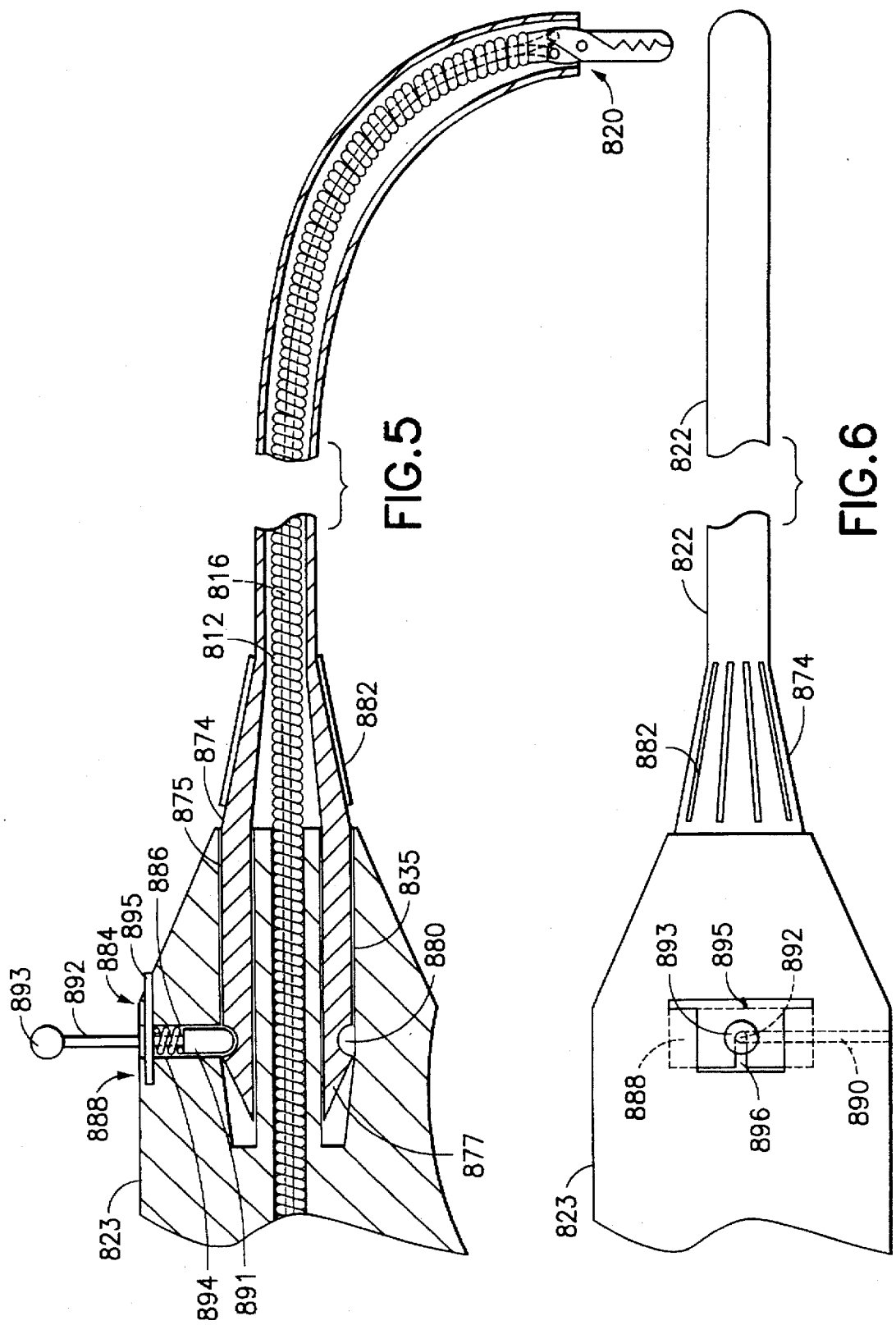

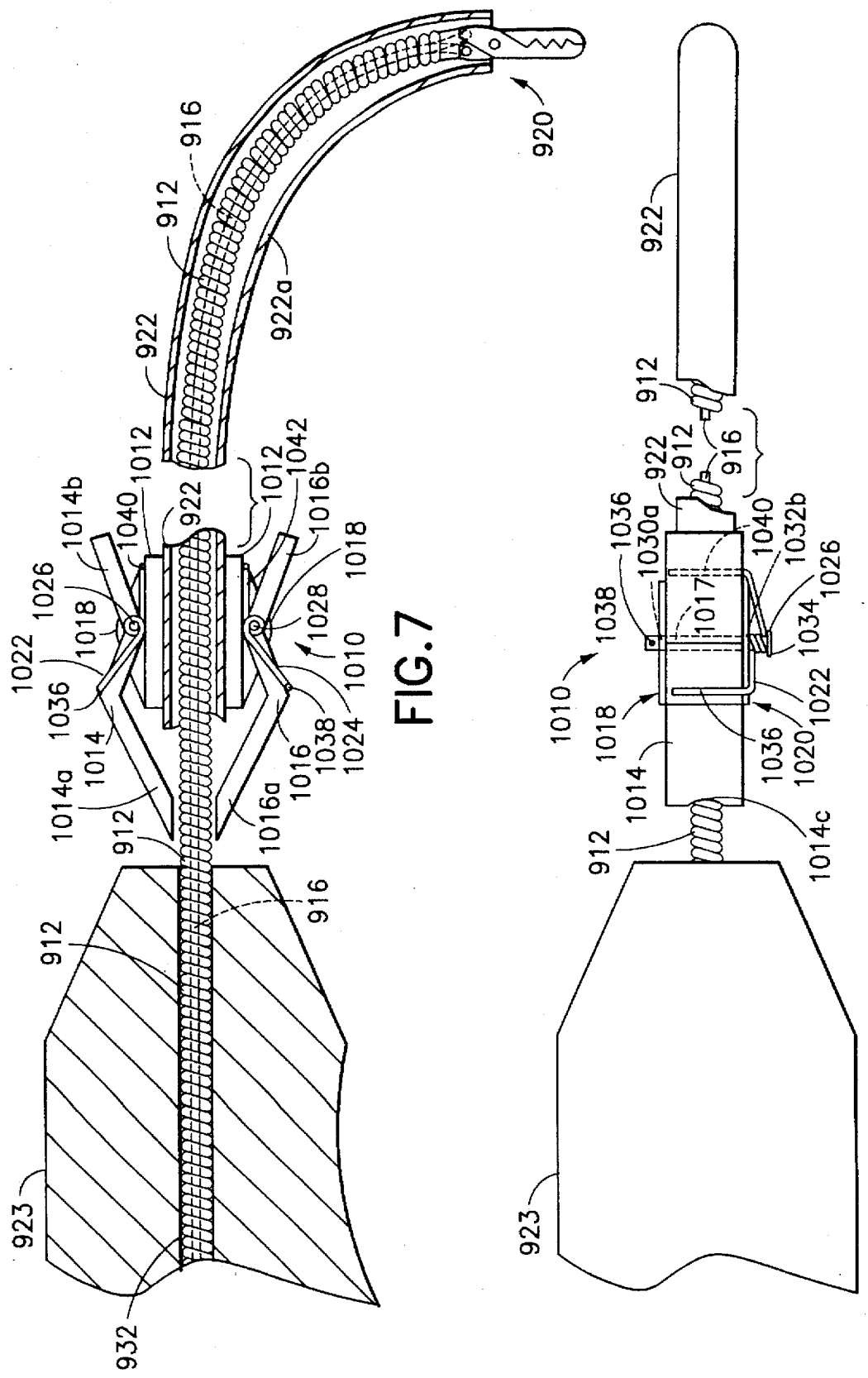

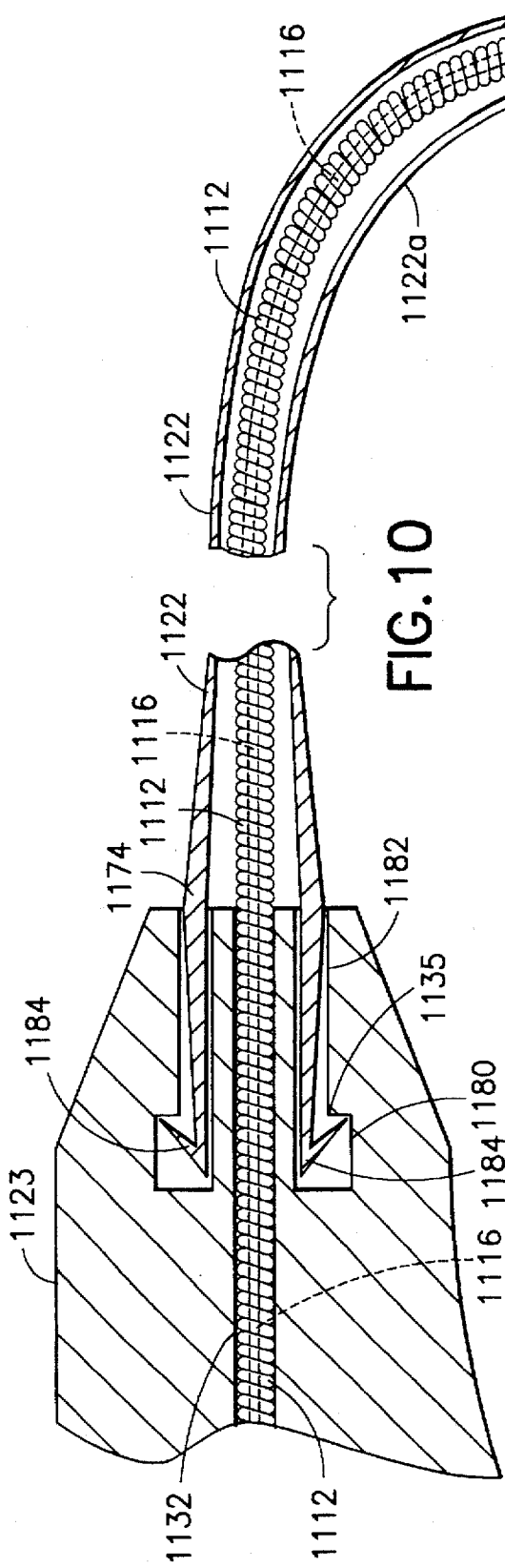
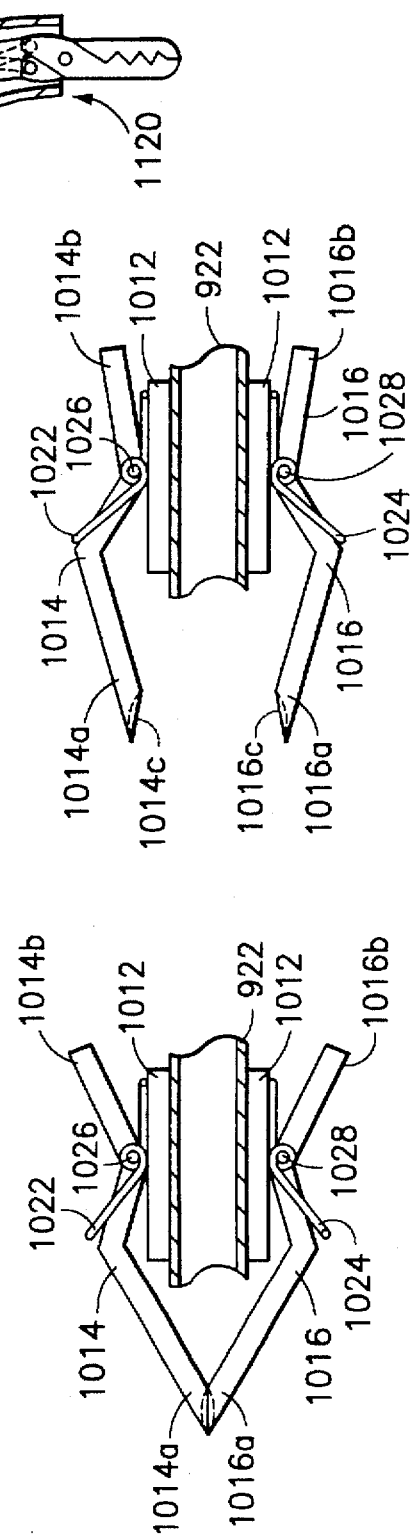

LAPAROSCOPIC INSTRUMENT KIT INCLUDING A PLURALITY OF RIGID TUBES

This application is related to co-owned U.S. Pat. No. 5,192,298, entitled "Disposable Laparoscopic Surgical Instruments", co-owned U.S. Pat. No. 5,478,350, entitled "Rack and Pinion Actuation Handle For Endoscopic Instruments", and co-owned U.S. Pat. No. 5,507,296, entitled "Radial Jaw Biopsy Forceps" which are hereby incorporated by reference herein in their entireties.

BACKGROUND OF THE INVENTION

1. Field of the Invention

This invention relates broadly to laparoscopic and arthroscopic surgical instruments. More particularly, this invention relates to surgical instruments used in laparoscopy and arthroscopy procedures which have substantially rigid tubes extending from the proximal handle end of the instruments.

2. State of the Art

An arthroscopic surgical instrument is an instrument used in a "minimally invasive" surgical repair of a joint. The arthroscopic instrument enables surgery at a joint without exposing the joint by a large incision. Arthroscopic surgical instruments generally include a proximal actuation handle coupled by a rigid tube and a control member to an end effector assembly. The end effector assembly typically includes a pair of jaws, scissors, forceps, or claps, at least one of the pair being rotatable relative to the other. The end effector and the distal end of the tube are introduced into the joint cavity through a small puncture or incision.

Laparoscopic surgical instruments are similar to arthroscopic instruments, but are passed through a small incision which provides access to the abdominal cavity. The incision is usually formed via the use of a trocar which is used to puncture the skin and fascia, and the laparoscopic instrument is passed through a trocar tube which remains in place in the incision. For purposes herein, the terms "arthroscopic" and "laparoscopic" shall be used interchangeably to refer to instruments passed through a small incision in the body, either with or without a trocar tube.

The end effector of the laparoscopic instrument can be located and manipulated at the surgical site by movement of the proximal end of the rigid tube and handle, as such movement will translate into predictable movement of the distal end. In this manner, the practitioner will be able to control the location of the end effector assembly after the end effector assembly and tubular portion of the instrument have been received into the body. Depending on the procedure to be performed, the rigid tube should either be straight or curved to most assist the practitioner in locating the end effector assembly at the desired surgical site. The degree to which the tube of the instrument may be required to be curved depends on the procedure being conducted and specifics of the surgical site. The proximal actuation handle is then used to operate the end effector by opening and closing the jaws, scissors, or other end effectors.

Various laparoscopic procedures have in the past required that the practitioner have a variety of instruments available, each having a tube curved to one degree or another. In this manner, the instrument which the practitioner believes to be most suitable for the surgical procedure may be chosen. However, having many instruments on hand is cumbersome. Furthermore, if during the procedure the practitioner needs an instrument having a tube with an alternate curvature, a new instrument must be utilized adding further expense to the procedure.

SUMMARY OF THE INVENTION

It is therefore an object of the invention to provide a laparoscopic surgical instrument kit wherein a single laparoscopic instrument can be used regardless of the desired or required curvature.

It is another object of the invention to provide a flexible laparoscopic surgical instrument with a plurality of rigid tubular members of varying curvature which can be removably coupled to the instrument.

It is a further object of the invention to provide a laparoscopic surgical instrument kit having a laparoscopic surgical instrument having a flexible tube and a plurality of rigid tubular members which are curved to different degrees, and which are easily coupled to and removable from the laparoscopic surgical instrument.

In accord with these objects which will be discussed in detail below, a laparoscopic surgical instrument includes an actuation handle, a control member, a flexible tubular member, a substantially rigid tubular member, and an end effector assembly. The control member extends through the flexible tubular member, and the actuation handle is coupled to the proximal ends of the control member and the flexible tubular member. The end effector assembly is coupled to the distal end of the control member and the flexible tubular member. The substantially rigid tubular member extends over substantially the entire flexible tubular member. The actuation handle is arranged to move the control member relative to the flexible tubular member, resulting in the operation of the end effector assembly. One or both of the rigid tubular member and the handle includes coupling means for removably coupling the rigid tubular member to either the actuation handle or the flexible tubular member. In accord with a preferred aspect of the invention, a set of rigid tubes is provided, wherein each of the rigid tubes is curved to a different degree.

It will be appreciated that when a rigid tube is extended over the flexible tube of the instrument, the flexible tube conforms to the shape of the rigid tube. If a rigid tube is curved, the flexible tube will extend through the rigid tube and create an instrument having a curved distal end. It will also be appreciated that when the instrument is supplied with a variety a rigid tubes, as in a surgical instrument kit, the practitioner is able to choose from the variety of rigid tubes the tube which is most appropriate for a procedure. The practitioner is further able to change the instrument from one having a rigid tube of a first curvature to one having a rigid tube of a second curvature by uncoupling the first rigid tube from the flexible instrument and coupling the second rigid tube thereto.

Additional objects and advantages of the invention will become apparent to those skilled in the art upon reference to the detailed description taken in conjunction with the provided figures.

BRIEF DESCRIPTION OF THE DRAWINGS

FIG. 2 an enlarged broken side elevation view in partial section of the embodiment of FIG. 1;

FIG. 3A is a cross section across line 3A—3A in FIG. 2;

FIG. 3B is a cross-section across line 3B—3B in FIG. 2;

FIG. 5 is a broken side elevation view in partial section of a third embodiment of the invention;

FIG. 6 is a top view in partial section of the embodiment of FIG. 5;

FIG. 7 is a broken side elevation view in partial section of a fourth embodiment of the invention;

FIG. 8 is a broken top view of the embodiment of FIG. 7;

FIGS. 9A and 9B are broken side elevation views in partial section of the embodiment of FIG. 7; and FIG. 10 is a broken side elevation view in partial section of a fifth embodiment of the invention.

DETAILED DESCRIPTION OF THE PREFERRED EMBODIMENTS

Figure 1:
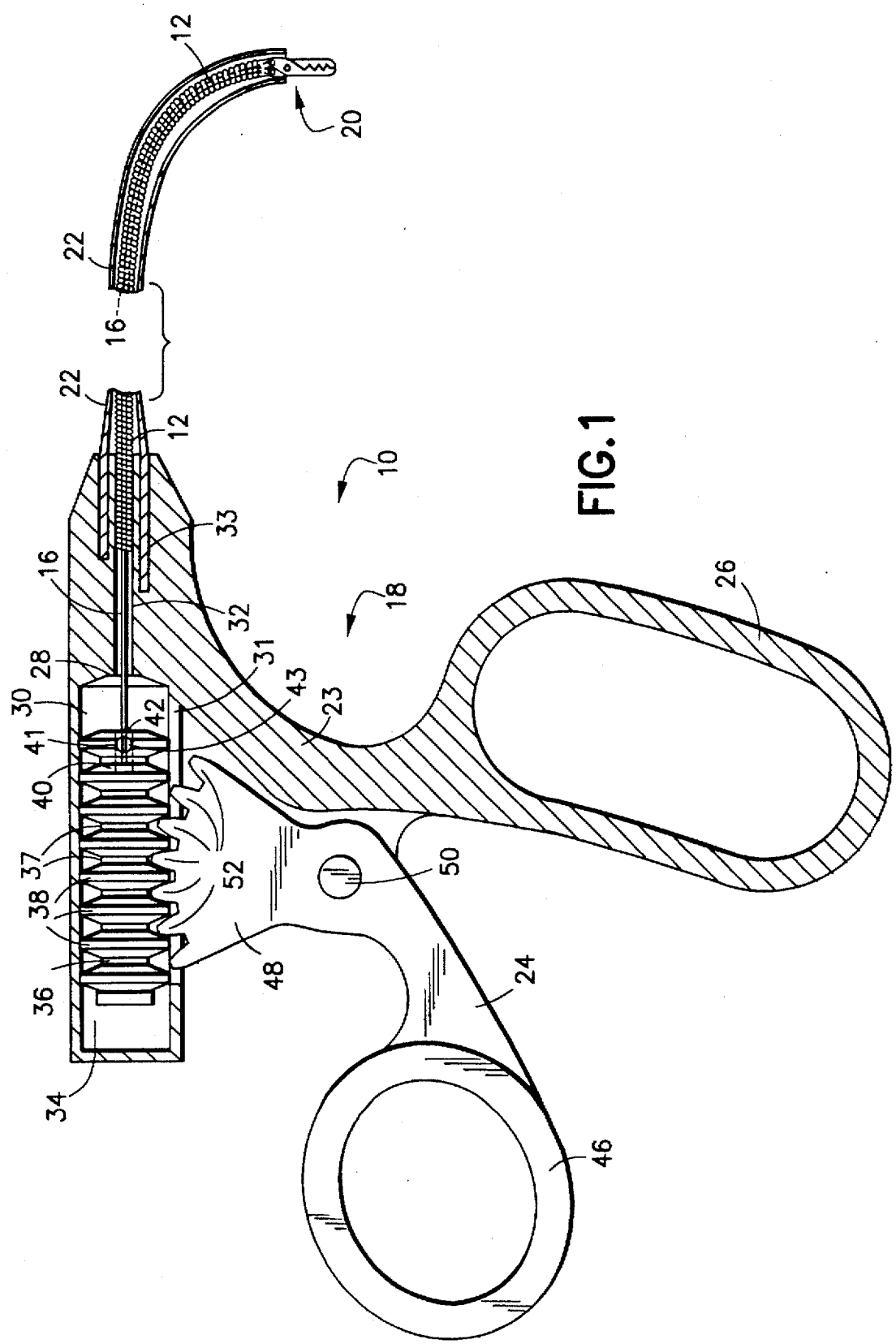
FIG. 1 is a broken side elevation view in partial section of a first embodiment of the laparoscopic instrument of the invention.

Turning now to FIGS. 1 and 2, a laparoscopic surgical instrument according to the invention 10 includes a flexible tube member or coil 12 having a lumen 14, a control member or control wire 16, a proximal actuation handle 18, an end effector 20, and a substantially rigid tubular member or tube 22. As discussed in more detail below, the coil 12 and control member 16 are coupled at their proximal ends to the actuation handle 18 and at their distal ends to the end effector 20, and the substantially rigid tubular member 22 extends over the flexible tubular member 12 and is coupled at its proximal end to the actuation handle 18.

The actuation handle 18 includes a stationary member 23, a lever (or movable member) 24, and a cylindrical rack member 36. The stationary member 23 has a stepped throughbore 28 having a larger diameter proximal portion 30 and a smaller diameter distal portion 32, a distal tube receiving slot 33, and a lower finger ring 26. The rack member 36 is slidably disposed within the proximal end 30 of the throughbore 28 and includes alternating cogs 38 and grooves 37 and an axial bore 42 for receiving the wire 16. The rack member also includes a lateral threaded bore 41 which extends into the axial bore. The lever 24 has an upper pinion portion 52 for engaging the cogs 38 and grooves 37 of the rack member 36, and a lower thumb ring 46. The lever 24 is pivotally coupled to the stationary member 23 by a coupling pin 50.

As seen in FIG. 1, the proximal end of the coil 12 is engaged in the distal end of the throughbore of the stationary member 23. The proximal end of the control wire 16 extends into the axial bore 42 of the rack member 36. A set screw 43 threaded into the lateral bore 41 secures the proximal end of the control wire 16 within the axial bore 42. The distal end of the control wire 16 extends through the coil 12, is split, and coupled to the end effector 20. The actuation handle is described in more detail in previously incorporated U.S. Pat. No. 5,478,350.

The end effector 20, shown in FIG. 2, generally includes a pair of identical forceps jaws 56, 58 and a clevis 60. Each jaw 56, 58 has a proximal tang 62, 64, teeth 66, 68, and a transverse bore 70. The clevis 60 is coupled to the distal end of the coil. The jaws 56, 58 are attached to the clevis 60 by a clevis pin 72 which passes through the transverse bore 70 of each jaw 56, 58. The split end of the control wire is coupled to the proximal tang 62, 64 of each jaw 56, 58. The forceps jaws of FIGS. 1 and 2 are described in more detail in previously incorporated U.S. Pat. No. 5,507,295. It will be appreciated that other end effectors can also be used, such as scissor blades, clamps, forceps, or other surgical end effectors.

It will be appreciated that by pivoting the lever 22 with respect to the stationary member 22, the pinion 52 moves the rack member 26 linearly within the throughbore. As the rack member 34 is moved linearly, the rack member effects a translational movement of the control wire relative to the coil, thereby actuating the end effectors.

Turning to FIGS. 2, 3A and 3B the distal tube receiving slot 33 of the stationary member 23 is shown to include an annular groove 35 extending proximally into the distal portion of the stationary member 23 and three identical slots 39a, 39b, 39c extending further proximally. The slots have the shape of a tubular segment (arced), and the center of each slot is located at 120° intervals around the circumference of the annular groove 35.

The substantially rigid tube 22 includes a preferably flared proximal end 74 having coupling flanges 76a, 76b, 76c, and a distal end 78. The coupling flanges 76a, 76b, 76c are identical tubular segments radially arranged and having their longitudinal centers separated by 120°. In the embodiment of FIGS. 1, 2, 3A and 3B, the coupling flanges are frictionally engaged in the arced slots 39a, 39b, 39c in the distal end of the stationary member 23 and the proximal end of the tube is seated in the annular groove 35. Engaging the coupling flanges into the arced slots prevents the tube from rotating with respect to the stationary member. In addition, having three identical slots substantially the same size as three identical flanges, and having the slots and flanges each with the same radial arrangement, permits the tube to be coupled to the stationary member in three positions, each position being 120° offset from the other.

As seen best in FIGS. 1 and 2, the rigid tube 22 has a curved portion 22a located near its distal end which has a larger diameter than the remainder of the tube. The larger diameter of the curvature allows the end effector increased clearance as the coil and end effector are pushed through the tube during engagement of the tube onto the handle.

Figure 4:
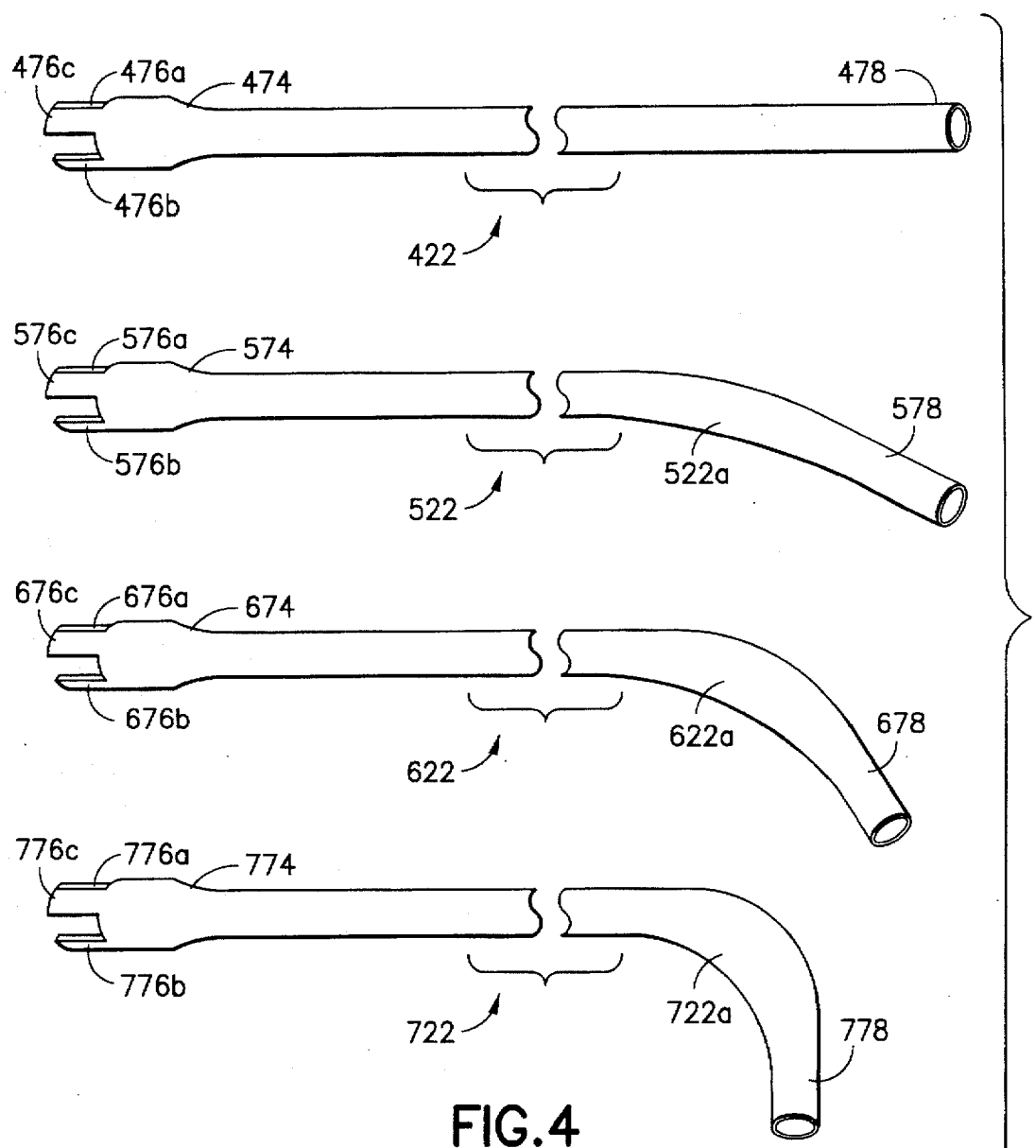
FIG. 4 is a side elevation view of a set of rigid tubes for use with a laparoscopic instrument kit according to a second embodiment of the invention.

According to a preferred aspect of the invention, the laparoscopic surgical instrument is supplied in a kit which includes a set of additional tubes. Each tube of the kit preferably has a curvature which differs from the curvature of the other tubes. Referring to FIG. 4, four tubes 422, 522, 622, 722 are shown. The first tube 422 has a flared proximal portion 474 with coupling flanges 476a, 476b, 476c, a distal end 478, and has a zero curvature; i.e. it is straight. As a result of the zero curvature, the distal end does not require a larger diameter for accommodating the end effector assembly through any bends. A second tube 522 substantially similar to the first tube has a gradual bend resulting in the distal portion 578 being 30° off axis from the proximal portion 574. The curved portion 522a has a wider diameter to accommodate the end effector (not shown) as it extends through the curved portion. This is because the end effector is not flexible and cannot easily conform to a narrow bend. A third tube 622 substantially similar to the second tube has a curved portion 622a resulting in the distal portion 678 being 60° off axis from the proximal portion 674. A fourth tube 722 substantially similar to the second tube has a curved portion 722a resulting in the distal portion 778 being 90° off axis from the proximal portion 774.

Turning now to FIGS. 5 and 6, another embodiment of the invention is shown, substantially similar to the first embodiment (with like parts having numbers incremented by 800). The difference between this embodiment and the first embodiment lies in the coupling of the tube 822 and the stationary member 823 of the instrument. In particular, the proximal portion of the tube includes thicker tube walls, a circumferential groove 880, and a tapered end 877 wherein the tube walls taper such that the outer diameter of the tube decreases, yet the inner diameter of the tube remains constant. The circumferential groove 880 is located in the tube wall where the wall is at maximum thickness. Distal of the circumferential groove 880 on the tube 822, the inner diameter of the tube gradually decreases to approach the outer diameter of the coil 812. The outer surface of the tube has a number of longitudinal ridges 882 engageable by a practitioner's finger.

The distal end of the stationary member 823 includes an annular groove 835 for receiving the proximal end of the tube 822 and a spring-loaded catch assembly 884 for engaging the circumferential groove 880 of the tube 822. The catch assembly 884 includes a number of slots and bores in the stationary member 823: a catch slot 886 extending radially into the stationary member and intersecting the annular groove 835, a T-shaped slot 888 extending into the distal end of the stationary member and perpendicular to and intersecting the catch slot 886, and a lateral bore 890. The catch assembly further includes a catch pin 891 for engaging the circumferential groove 880 of the tube, a spring 894, and a slotted cover 895. The catch pin 891 includes a handle 892 and a knob 893. The spring 894 is positioned around the handle 892 of the catch pin. It is preferable that the spring 894 have an inner diameter larger than the knob 893, but an outer diameter smaller than the catch slot 886, allowing the spring to easily fit over the knob and sit on the catch pin 891 within the catch slot 886. The catch pin 891 and spring 894 are placed into the catch slot 886 and the cover 895 is frictionally engaged into the T-shaped slot 888. The cover 895 is provided with a handle slot 896 which fits around the handle 892 of the catch pin. The handle slot 896 is also small enough to allow the cover to secure the spring within the catch slot 886. A lateral bore 890 is available for inserting a tool, such as a pin, into the lateral bore and further into the catch slot to hold down the spring while the cover is engaged into the T-shaped slot.

It will be appreciated that when the tube 822 is received into the annular groove 835, the tapered end 877 of the tube will contact the catch pin 891 and automatically lift the catch pin until the catch pin snaps into the circumferential groove 880 of the tube 822, thereby securing the tube in the stationary member 823 of the handle. The tube is rotatable relative to the stationary member as the tube may rotate on its axis in the annular groove and yet be engaged within the stationary member by the catch pin. The ridges 882 on the tube allow a practitioner's fingers to engage the tube and rotate the curved distal portion of the tube into a position required for the procedure. It will be further appreciated that the tube 823 may be disengaged from the catch assembly 884 by lifting the knob 893 or handle 892 of the catch pin 891, thereby allowing the tube 822 to be pulled out of the distal end of the stationary member 823 of the instrument. Another tube may then be inserted into the annular groove 835.

Turning now to FIGS. 7, 8, 9A, and 9B, another embodiment of the invention is shown. This embodiment is substantially similar to the first embodiment (with like parts having numbers incremented by 900). In this embodiment, the substantially rigid tube 922 is coupled to the coil 912, as opposed to the handle of the flexible surgical instrument. In particular, a proximal coupling assembly 1010 couples the tube 922 to the coil 912. The proximal coupling assembly 1010 includes a relatively short tubular body 1012, two clamps arms 1014, 1016, two side braces 1018, 1020, two leaf springs 1022, 1024, and two pivot pins 1026, 1028. Each side brace 1018, 1020 has two ends, and provided at each end is a transverse bore 1030a, 1030b, 1032a, 1032b for receiving a pivot pin 1026, 1028. The side braces 1018, 1020 are positioned on diametrically opposing sides of the tubular body 1012. Each clamp arm 1014, 1016 includes a proximal engaging end 1014a, 1016a, a distal lever end 1014b, 1016b and a transverse bore 1017, 1019 for receiving a pivot pin. The clamp arms 1014, 1016 are positioned on diametrically opposed sides of the tubular body 1012, perpendicular to the side braces 1018, 1020. The braces and clamp arms are held in position by the pivot pins 1026, 1028. One pivot pin 1026 extends through a transverse bore 1030a at a first end of one side brace 1018, through the transverse bore 1017 in a first clamp arm 1014, and through a transverse bore 1032a at a first end of the other side brace 1020. The other pivot pin 1028 extends through a transverse bore 1030b at a second end of one side brace 1018, through the transverse bore 1019 in a second clamp arm 1016, and through a transverse bore 1032b at a second end of the other side brace 1020. The pivot pins 1026, 1028 are each provided at one end with a head 1034, having a larger diameter than the transverse bores in the side braces, and at the other end with a diametric bore 1036, having a cotter pin 1038 situated therein (FIG. 8). A leaf spring 1022, 1024 is situated around each pivot pin 1026, 1028 and has a first arm 1036, 1038 extending against the clamp arm 1014, 1016 and second arm 1040, 1042 extending against the tubular body 1012. The leaf springs 1022, 1024 are tensioned such that the clamp arms are urged by the springs toward each other. The engaging ends 1014a, 1014b of the clamp arms are provided with an arced cutout 1014c, 1016c, such that when the arced cutouts contact the coil 912, greater surface area contact is made between the clamp arms and the coil (FIG. 8). The coupling assembly 1010 is coupled to the proximal end of the rigid tube 922 preferably by an interference fit and/or by gluing. However, the tubular body 1012 of the coupling assembly 1010 and the proximal end of the tube may also be coupled by other means, for example, by threading together, welding, etc.

As illustrated in FIGS. 9A and 9B, when the coupling assembly 1010 is not coupled to a coil 912, the engaging ends 1014a, 1016a of the clamp arms 1014, 1016 are urged toward each such that they will contact each other. When a practitioner's fingers apply force to the lever ends 1014b, 1016b of the clamp arms, the clamp arms pivot about the coupling pins 1026, 1028, thereby moving the engaging ends away from each other, and positioning the coupling assembly in an open position. The end effector 920 and coil 912 can then be inserted between the engaging ends of the clamp arms, through the tubular body 1012 of the coupling assembly and through the tube. As the clamp arms are released, they will clamp down on the coil and hold the tube in position against the coil. It will be appreciated that at any time the coupling assembly may then be disengaged from the coil by moving the clamp arms into the open position. The rigid tube may then be removed from the flexible instrument by sliding the tube distally relative to the instrument. Another tube (typically of different curvature) with a coupling means may then be slid over the distal end of the flexible instrument and engaged to the coil or handle of the flexible instrument.

Referring to FIG. 10, another embodiment of the invention is shown. This embodiment is substantially similar to the first embodiment (with like parts having numbers incremented by 1100) except that the instrument is provided with a rigid tube which is intended to be placed on and non-removably coupled to the stationary member (handle) of the instrument by the practitioner. The stationary member 1123 includes a stepped annular groove 1135 having a proximal portion 1180 with larger diameter and a distal portion 1182 with a smaller diameter. The proximal end of the tube 1122 includes an annular barb 1184, wherein the barb is angled outwardly and distally. It will be appreciated that as the proximal end 1174 of the tube is inserted into the annular groove 1135, the barb 1184 is flattened against the wall of distal portion 1182 of the annular groove. As the tube is moved into the proximal portion 1180 of the annular groove 1135, the annular barb 1184 is released into the proximal portion of the groove and prevents the tube from being disengaged.

There have been described and illustrated herein several embodiments of a laparoscopic surgical instrument. While particular embodiments of the invention have been described, it is not intended that the invention be limited thereto, as it is intended that the invention be as broad in scope as the art will allow and that the specification be read likewise. Thus, while particular mechanisms and methods of removably coupling the tube to the instrument have been disclosed, including friction fits and spring loaded catches and claps, it will be understood that other mechanisms and methods of coupling the tubes to the actuation handle or coil can be used wherein the tubes are either rotatably, non-rotatably, disengageably or non-disengageably coupled. Furthermore, while in some embodiments the tube has been shown to have a greater diameter at the proximal end to thereby allow easier insertion of the coil through the proximal end of the tube, it will be appreciated that it is not always necessary for the tube to have a greater diameter at the proximal end. In addition, while a kit of four rigid tubes has been shown for use with a single instrument, it will be appreciated that any number of tubes can be included in a kit, wherein each tube preferably has a different curvature. Also, while a particular type of actuation handle has been disclosed, it will be understood that another handle can be used which likewise imparts translational movement of the control wire relative to the coil. For example, other actuation handles are described in detail in co-owned U.S. Pat. Nos. 5,192,298 and 5,507,296. Furthermore, while the instrument has been shown to include one control wire, split at the distal end for attachment to the tangs of the jaws, it will be recognized that one or two control wires can be used wherein each control wire is coupled to one tang of a jaw, scissors, clamp, or forceps. It will therefore be appreciated by those skilled in the art that yet other modifications can be made to the provided invention without deviating from its spirit and scope as so claimed.

We claim:

1. A laparoscopic surgical instrument, comprising:
   a) a flexible tubular member;
   b) a control member extending through said flexible tubular member;
   c) an end effector coupled to said control member and said flexible tubular member;
   d) an actuation handle coupled to said control member and said flexible tubular member for moving said control member and said flexible tubular member relative to each other so as to effect movement of said end effector; and
   e) a substantially rigid tubular member extending over substantially all of said flexible tubular member distal of said actuation handle, said end effector extending distally beyond said substantially rigid tubular member, said substantially rigid tubular member being coupled to one of said flexible tubular member and said actuation handle.

2. A laparoscopic surgical instrument according to claim 1, wherein:
   said substantially rigid tubular member includes a curved distal portion.

3. A laparoscopic surgical instrument according to claim 2, wherein:
   said substantially rigid tubular member has a first diameter along substantially all of its length and a second diameter at said curved distal portion which is larger than said first diameter.

4. A laparoscopic surgical instrument according to claim 1, wherein:
   said substantially rigid tubular member is removably coupled to one of said flexible tubular member and said actuation handle.

5. A laparoscopic surgical instrument according to claim 1, wherein:
   said substantially rigid tubular member is rotatably coupled to one of said flexible tubular member and said actuation handle.

6. A laparoscopic surgical instrument according to claim 1, wherein:
   said substantially rigid tubular member has a first diameter along substantially all of its length and a second diameter at its proximal end which is larger than said first diameter.

7. A laparoscopic surgical instrument according to claim 1, wherein:
   said substantially rigid tubular member has a plurality of flanges at its proximal end and said actuation handle has a plurality of slots which receive said plurality of flanges.

8. A laparoscopic surgical instrument according to claim 1, wherein:
   said substantially rigid tubular member has a barb at a proximal end and said actuation handle has a groove for receiving said barb.

9. A laparoscopic surgical instrument according to claim 1, wherein:
   said actuation handle further comprises an annular receiving slot and a catch assembly, and said substantially rigid tubular member includes a circumferential groove at a proximal end,
   wherein said substantially rigid tubular member is received into said annular receiving slot and said catch assembly removably engages with said circumferential groove.

10. A laparoscopic surgical instrument according to claim 1, wherein:
    said flexible tubular member is a flexible metal coil.

11. A laparoscopic surgical instrument according to claim 1, further comprising:
    f) a coupling means for coupling said substantially rigid tubular member to said flexible tubular member,
    wherein said coupling means is coupled to said proximal end of said substantially rigid tubular member and is removably coupled to said flexible tubular member.

12. A surgical instrument kit, comprising:
    a) a flexible tubular member;
    b) a control member extending through said flexible tubular member;
    c) an actuation handle coupled to said control member and said flexible tubular member for moving said control member and said flexible tubular member relative to each other;

d) an end effector coupled to said control member and said flexible tubular member; and e) a plurality of substantially rigid tubular means for extending over said flexible tubular member and coupling to one of said tubular member and said actuation handle.

13. A surgical instrument kit according to claim 12, wherein:

at least one of said plurality of substantially rigid tubular means includes a curved portion.

14. A surgical instrument kit according to claim 12, wherein:

none of said plurality of substantially rigid tubular means is identical to another of said plurality of substantially rigid tubular means.

15. A surgical instrument kit according to claim 12, wherein:

said plurality of substantially rigid tubular means are for removably coupling to said actuation handle.

16. A surgical instrument kit according to claim 12, wherein:

said plurality of substantially rigid tubular means are for rotatably coupling to said actuation handle.

17. A surgical instrument kit according to claim 12, further comprising:

f) coupling means provided on at least one of said actuation handle and each of said plurality of substantially rigid tubular means for removably coupling said plurality of substantially rigid tubular means to said actuation handle.

18. A surgical instrument kit according to claim 17, wherein:

said coupling means comprises an opening in a distal end of said actuation handle which receives each of said plurality of substantially rigid tubular means in a friction fit manner.

19. A surgical instrument kit according to claim 17, wherein:

said coupling means comprises a circumferential groove on a proximal end of each of said plurality of substantially rigid tubular means and spring loaded means in said actuation handle for removable engaging said circumferential groove.

20. A surgical instrument kit according to claim 12, wherein:

said flexible tubular member is a coil, and said surgical instrument kit further comprises f) coupling means provided on each of said plurality of substantially rigid tubular means for removably coupling said plurality of substantially rigid tubular means to said coil.

\* \* \* \* \*